US006316269B1

(12) United States Patent
Tsai et al.

(10) Patent No.: US 6,316,269 B1
(45) Date of Patent: Nov. 13, 2001

(54) METHODS FOR SCREENING DRUGS TO PREDICT TARDIVE DYSKINESIA

(75) Inventors: Guochuan Tsai; Xudong Huang, both of Cambridge; Ashley I. Bush, Sommerville, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/166,594

(22) Filed: Oct. 6, 1998

Related U.S. Application Data

(60) Provisional application No. 60/060,962, filed on Oct. 6, 1997.

(51) Int. Cl.[7] .......................... G01N 33/00; G01N 21/75; G01N 33/53; C12Q 1/00; A61K 43/40
(52) U.S. Cl. ........................ 436/135; 435/4; 435/7.1; 436/127; 436/131; 436/166; 436/172; 436/501; 436/518; 514/171; 514/327; 514/410; 514/561; 514/565; 514/665
(58) Field of Search ............................ 514/327, 410, 514/171, 561, 565, 665; 435/21, 7.2, 4; 436/501, 518, 127, 131, 135, 166, 172

(56) References Cited

U.S. PATENT DOCUMENTS

| 5,602,150 | 2/1997 | Lidsky | 514/327 |
| 5,927,283 | 7/1999 | Abraham et al. | 128/898 |

FOREIGN PATENT DOCUMENTS

| WO 96/07096 | 3/1996 | (WO) . |
| WO 98/40071 | 9/1998 | (WO) . |
| WO 99/18432 | 4/1999 | (WO) . |

OTHER PUBLICATIONS

Bevan et al. Trends in Biotech., vol. 13, No. 3, pp. 115–121, 1995.*
Atwood, C.S. et al., "Role of Free Radicals and Metal Ions in the Pathogenesis of Alzheimer's Disease," in *Metal Ions in Biological Systems*, Sigel, A. and Sigel H., eds., vol. 36, Ch. 10, Marcel Dekker, Inc., New York, pp. 309–364 (1999).
Huang, X., et al., "The Aβ Peptide of Alzheimer's Disease Directly Produces Hydrogen Peroxide through Metal Ion Reduction," *Biochem.* 38:7609–7616, American Chemical Society (Jun. 1999).
McKeon–O'Mally, C., et al., "Potential Therapeutic Targets for Alzheimer's Disease," *Emerging Therapeutic Targets* 2:157–179, Ashley Publications Ltd. (Feb. 1998).
International Search Report for PCT/US00/11715, mailed Aug. 30, 2000.
Barton, A. et al., "Low Plasma Iron Status and Akathisia," *Journal of Neurology, Neurosurgery and Psychiatry* 53:671–674 (1990).

Bowie, J. et al., "Plasma Zinc and Akathisia," *Trace Elements in Medicine* 7:166–168 (1990).
Burki, H. R. et al., "Biochemical Methods for Predicting the Occurrence of Tardive Dyskinesia," *Communications in Psychopharmacology* 3:7–15 (1979).
Gunne, L. M. et al., "A Monitoring Test for the Liability of Neuroleptic Drugs to Induce Tardive Dyskinesia," *Psychopharmacology* 63:195–198 (1979).
Ogawa, T. et al., "Tardive Dyskinesia and Neurotransmitters: Effects of Sodium Valproate, Cyproheptadine, Oxypertine, Hydroxyzine Pamoate and Ca–hopantenate on Monoamine Metabolites, Cyclic Nucleotides and Gamma–Aminobutyric Acid in Human Cerebrospinal Fluid," *Clinical Therapeutics* 7:1–17 (1984).
Yokoyama, H. et al., "In Vivo Analysis of Hydrogen Peroxide and Lipid Radicals in the Striatum of Rats Under Long–Term Administration of a Neuroleptic," *Free Radical Biology & Medicine* 24:1056–1060 (1998).
Adler, L.A., et al., "Vitamin E Treatment of Tardive Dyskinesia," *Am. J. Psychiatry* 150:1405–1407 (1993).
Andersson, U., et al., "Reduced Glutamate Decarboxylase Activity in the Subthalamic Nucleus in Patients with Tardive Dyskinesia," *Movement Disorders* 4:37–46 (1989).
Biaglow, J.E. and A.V. Kachur, "The Generation of Hydroxyl Radicals in the Reaction of Molecular Oxygen with Polyphosphate Complexes of Ferrous Ion," *Radiation Res.* 148:181–187 (Aug. 1997).
Burkhardt, C., et al., "Neuroleptic Medications Inhibit Complex I of the Electron Transport Chain," *Annals of Neurology* 33:512–517 (1993).
Cadet, J.L. and J.B. Lohr, "Possible Involvement of Free Radicals in Neuroleptic–Induced Movement Disordes," *Annals NY Acad. Sci.* 570:176–185 (1989).
Christensen, E., et al., "Neuropathological Investigation of 28 Brains from Patients with Dyskinesia," *Acta Psychiatrica Scandinavica* 46:14–23 (1970).

(List continued on next page.)

Primary Examiner—Jyothsna Venkat
Assistant Examiner—Maurie E. Garcia
(74) Attorney, Agent, or Firm—Sterne, Kessler, Goldstein & Fox, P.L.L.C.

(57) ABSTRACT

The present invention provides screening methods for identifying compounds which induce tardive dyskinesia (TD) when administered to an animal. In particular, the methods involve assaying for intermediates and end products of reactions associated with candidate compound mediated reduction of reducible substrates. Also provided are high-throughput screening methods for determining whether compounds induce TD when administered to an animal. Further, provided are methods for treating psychoses comprising testing antipsychotic drugs to identify those which will not induce TD when administered to an animal and administering one or more such drugs to a patient in need thereof.

16 Claims, 12 Drawing Sheets

OTHER PUBLICATIONS

Coyle, J.T. and P. Puttfarcken, "Oxidative Stress, Glutamate, and Neurodegenerative Disorders," *Science* 262:689–695 (1993).

Crow, T.J., et al., "Abnormal Involuntary Movements in Schizophrenia: Are They Related to the Disease Process of Its Treatment? Are They Associated with Changes in Dopamine Receptors?" *J. Clin. Pyschopharmacol.* 2:336–340 (1982).

Egan, M.F. et al., "Treatment of Tardive Dyskinesia with Vitamin E," *Am. J. Psychiatry* 149:773–777 (1992).

Goff, D.C., et al., "Tardive Dyskinesia and Substrates of Energy Metabolism in CSF," *Am. J. Psychiatry* 152:1730–1736 (1995).

Gunne, L.M., et al., "Association with persistent neuroleptic–induced dyskinesia of regional changes in brain GABA synthesis," *Nature* 309:347–349 (1984).

Gunne, L.M. and J.–E. Häggström, "Experimental Tardive Dyskinesia," *Clin. Psychiatry* 46:48–50 (1985).

Gunne, L.M. and P.E. Andrén, "An Animal Model for Coexisting Tardive Dyskinesia and Tardive Parkinsonism: A Glutamate Hypothesis for Tardive Dyskinesia," *Clin. Neuropharmacol.* 16:90–95(1993).

Gutteridge, J.M.C. and S. Wilkins, "Copper Salt–Dependent Hydroxyl Radical Formation Damage to Proteins Acting as Antioxidants," *Biochimica et Biophysica Acta* 759:38–41 (1983).

Han, J.C. and G.Y. Han, "A Procedure for Quantitative Determination of Tris(2–carboxyethyl) phosphine, an Odorless Reducing Agent More Stable and Effective than Dithiothreitol," *Anal. Biochem.* 220:5–10 (1994).

Han, J., et al., "Quantitation of Hydrogen Peroxide Using Tris(2–carboxyethyl)phosphine," *Anal. Biochem.* 234:107–109 (Feb. 1996).

Hoffer, A., "Tardive dyskinesia treated with manganese," *Canadian Medical Assoc. J.* 117:859 (1977).

Huang, C.–C., et al., "Progression after chronic manganese exposure," *Neurology* 43:1479–1483 (1993).

Jackson–Lewis, V. and S. Przedborski, "Neuroleptic Medications Inhibit Complex I of the Electron Transport Chain," *Annals of Neurology* 35:244–245 (1994).

Jenner, P. and C.D. Marsden, "Is the dopamine hypothesis of tardive dyskinesia completely wrong?" *TINS* 9:259–260 (1986).

Jeste, D.V., et al., "Study of neuropathological changes in the striatum following 4, 8, and 12 months of treatment with fluphenazine in rats," *Psychopharmacol.* 106:154–160 (1992).

Kelm, M., et al., "The Nitric Oxide/Superoxide Assay," *J. Biol. Chem.* 272:9922–9932 (Apr. 1997).

Kojima, S., et al., "Antioxidative Activity of Benzylidene-ascorbate and its Effect on Adriamycin–Induced Cardiotoxicity," *Anticancer Res.* 14:1875–1880 (1994).

Lamont, L.S., "Beta–blockers and Their Effects on Protein Metabolism and Resting Energy Expenditure," *J. Cardiopulmonary Rehabil.* 15:183–185 (1995).

Landers, J.W. and B. Zak, "Determination of Serum Copper and Iron in a Single Small Sample," *Am. J. Clin. Path.* 29:590–592 (1958).

Lavoie, J.–C. and P. Chessex, "Bound Iron Admixture Prevents the Spontaneous Generation of Peroxides in Total Parenteral Nutrition Solutions," *J. Pediatric Gastroenterology and Nutrition* 25:307–311 (Sep. 1997).

Lee, C. and E. Okabe, "Hydroxyl Radical–Mediated Reduction of $Ca^{2+}$ –ATPase Activity of Masseter Muscle Sarcoplasmic Reticulum," *Jpn. J. Pharmacol.* 67:21–28 (1995).

Lemaire, P. and D.R. Livingstone, "Aromatic Hydrocarbon Quinone–mediated Reactive Oxygen Species Production in Hepatic Microsomes of the Flounder (*Platichthys flesus* L.)," *Comp. Biochem. Physiol.* 117C:131–139 (Jun. 1997).

Lohr, J.B., et al., "Increased Indices of Free Radical Activity in the Cerebrospinal Fluid of Patients with Tardive Dyskinesia," *Biol. Psychiatry* 28:535–539 (1990).

Markesbery, W.R., "Oxidative Stress Hypothesis in Alzheimer's Disease," *Free Radical Biol. and Med.* 23:134–147 (May 1997).

Masuoka, N., et al., "Spectrophotometric determination of hydrogen peroxide: catalase activity and rates of hydrogen peroxide removal by erythrocytes," *Clinica Chimica Acta* 254:101–112 (Oct. 1996).

Mion, C.C., et al., "MRI Abnormalitites in Tardive Dyskinesia," *Psychiatry Res:Neuroimaging* 40:157–166 (1991).

Mitchell, I.J. et al., "Glutamate–Induced Apoptosis Results in a Loss of Striatal Neurons in the Parkinsonian Rat," *Neurosci.* 63:1–5 (1994).

Morgenstern, H. and W.M. Glazer, "Identifying Risk Factors for Tardive Dyskinesia Among Long–term Outpatients Maintained with Neuroleptic Medications," *Arch. General Psychiatry* 50:723–733 (1993).

Nielsen, E.B. and M. Lyon, "Evidence for Cell Loss in Corpus Striatum After Long–Term Treatment with a Neuroleptic Drug (Flupenthixol) in Rats," *Psychopharmacol.* 59:85–89 (1978).

Olney, J.W., "Excitotoxic Amino Acids and Neuropsychiatric Disorders," *Annu. Rev. Pharmacol. Toxicol.* 30:47–71 (1990).

Pakkenberg, H., et al., "The Long–Term Effect of Perphenazine Enanthate on the Rat Brain. Some Metabolic and Anatomical Observations," *Psychopharmacologia* 29:329–336 (1973).

Pall, H.S., et al., "Evidence of Enhanced Lipid Peroxidation in the Cerebrospinal Fluid of Patients Taking Phenothiazines," *The Lancet* vol. II of 1987:596–599 (1987).

Peyser, C.E., et al., "Trial of d–α–Tocopherol in Huntington's Disease," *Am. J. Psychiatry* 152:1771–1775 (1995).

Rastogi, S.K., et al., "Behavioral and Biochemical Alterations Following Haloperidol Treatment and Withdrawal: The Animal Model of Tardive Dyskinesia Reexamined," *Progress in Neuro–Psychopharmacol. and Biological Psychiatry* 7:153–164 (1983).

Rothstein, J.D., et al., "Abnormal Excitatory Amino Acid Metabolism in Amyotrophic Lateral Sclerosis," *Annals of Neurology* 28:18–25 (1990).

Sayre, L.M., "Alzheimer's Precursor Protein and the Use of Bathocuproine for Determining Reduction of Copper (II)," *Science* 274:1933–1934 (Dec. 1996).

Shen, X.–M., et al., "Oxidation of Dopamine in the Presence of Cysteine: Characterization of New Toxic Products," *Chem. Res. Toxicol.* 10:147–155 (Feb. 1997).

Tsai, G. and J.T. Coyle, "N–Acetylaspartate in Neuropsychiatric Disorders," *Progress in Neurobiol.* 46:531–540 (1995).

Volterra, A., et al., "Glutamate Uptake Inhibition by Oxygen Free Radicals in Rat Cortical Astrocytes," *J. Neuroscience* 14:2924–2932 (1994).

Zak, B., "Simple Procedure for the Single Sample Determination of Serum Copper and Iron," *Clinica Chimica Acta* 3:328–334 (1958).

Zeller, J.M. and B.L. Sullivan, "C–reactive protein selectively enhances the intracellular generation of reactive oxygen products by IgG–stimulated monocytes and neutrophils," *J. Leukocyte Biol.* 52:449–455 (1992).

\* cited by examiner

METHODS FOR SCREENING DRUGS TO PREDICT TARDIVE DYSKINESIA

This application claims the benefit of the filing date of provisional application 60/060,962, filed on Oct. 6, 1997, which is herein incorporated by reference.

BACKGROUND OF THE INVENTION

1. Field of the Invention

The present invention provides a screening method for identifying compounds which induce tardive dyskinesia (TD) when administered to an animal.

2. Related Art

Tardive dyskinesia (TD) is a debilitating side effect of long-term antipsychotic exposure. This movement disorder affects 20–40% or more of patients treated chronically with antipsychotic drugs (Morgenstern, H. and Glazer, W. M., et al., *Arch. Gen. Psychiat.* 50:723–733 (1993)) and roughly 4–5% of patients are expected to develop TD with each year of antipsychotic treatment. The manifestations of TD may include adventitious movements of the oral-facial region, choreoathetosis of extremities and lordotic posturing. Despite the recent arrival of atypical antipsychotics such as clozapine and olanzapine, large numbers of patients continue to receive conventional antipsychotics.

The pathophysiologic basis for antipsychotic-induced TD remains unclear. While the theory that striatal postsynaptic dopamine receptor supersensitivity causes TD has been widely accepted for two decades, some evidence contradicts this model (Jenner, P. and Marsden, C. D., *TINS* 9:259–260 (1986)). Although acute administration of antipsychotics temporarily increases the firing of dopamine neurons, chronic antipsychotic treatment leads to a decrease in their firing rate due to depolarization blockage (Cadet, J. L. and Lohr, J. B., *Ann. N.Y. Aca. Sci.* 570:176–185 (1989)). After an acute elevation of dopamine turnover with haloperidol treatment, dopamine synthesis and release decreases; and dopamine metabolite levels return to normal with chronic treatment (Rastogi, S. K., et al., *Prog. Neuro-Psychopharmacol. & Biol. Psychiat.* 7:153–164 (1983)). Notably, striatal dopamine metabolites are reduced in monkeys with dyskinesia due to long-term antipsychotic treatment. Finally, post mortem neurochemical studies have not revealed a correlation between dopamine receptor up-regulation and TD (Crow, T. J., et al., *Journal of Clinical Psychopharmacology* 2:336–340 (1982). Thus, excessive activation of postsynaptic striatal dopamine receptors is not consistent with the time course nor persistence of TD.

An alternative hypothesis supports a neurodegenerative process affecting striatal efferent neurons analogous to Huntington's disease and Wilson's disease. TD is similar to these diseases in that all three diseases present choreoathetoid movements and pathological changes in the striatum. Christensen et al. (Christensen, E., et al., *Acta Psychiatrica Scandinavica* 46:14–23 (1970)) reported neuronal loss in the basal ganglia of patients with persistent TD; similar losses have been described in rats treated chronically with antipsychotics (Pakkenberg, H., et al., *Psychopharmacologia* 29:329–336 (1973); Nielsen, E. B. and Lyon, M., *Psychopharmacology* 59:85–89 (1978); Gunne, L. M. and Andren, P. E., *Clin. Neuropharmacol.* 16:90–95 (1993)). Importantly, loss of the presynaptic markers for the striatal-pallidal and nigral GABAergic neurons, glutamic acid decarboxylase (GAD) and γ-aminobutyric acid (GABA), have been observed in a primate model for TD and in post mortem studies of patients with TD (Gunne, L. M., et al., *Nature* 309:347–349 (1984); Gunne, L. M. and Haggstrom, J. E., *Journal of Clinical Psychiatry* 46:48–50 (1985); Anderson, U., et al., *Movement Dis.* 4:37–46 (1989)).

Both preclinical and clinical studies point to degeneration of striatal efferent neurons, especially GABAergic neurons, in TD. Although inconclusive, one brain imaging study has revealed reduction in the volume of the caudate nuclei in patients with TD in comparison to patients without TD and normal controls (Mion, C. C., el al., *Psychiatry Research* 40:157–166 (1991)). In the primate model of experimental TD, antipsychotic induced dyskinetic monkeys exhibit a reduction in presynaptic GABAergic markers in the subthalamic nucleus, the medial segment of globus pallidus and rostral part of the substantia nigra (Gunne, L. M., et al., *Nature* 309:347–349 (1984)). Rodent models of TD have also revealed a significantly lower density of large neurons in the striatum (Jeste, D. V., et al., *Psychopharmacology* 106:154–160 (1992)), and decreased GAD activity in the substantia nigra (Gunne, L. M. and Haggstrom, J. E., *Journal of Clinical Psychiatry* 46:48–50 (1985); Jester D. V., el al., *Psychopharmacology* 106:154–160 (1992)). Finally, Mitchell et al. have recently demonstrated rat apoptotic neuronal death in the striatum as a consequence of removal of the nigrostriatal dopaminergic pathway, similar to antipsychotic drug induced dopamine antagonism (Mitchell, I. J., et al., *Neuroscience* 63:1–5 (1994)).

We have found elevated levels of CSF N-acetylaspartate (NAA) in TD patients. This finding is consistent with a neuronal degenerative process since CSF NAA, a marker for neuronal integrity, is elevated in amyotrophic lateral sclerosis (Rothstein, J. D., et al., *Ann. Neurol.* 28:18–25 (1990)); and tissue NAA levels decrease in areas involved in active neuronal degeneration in amyotrophic lateral sclerosis, Huntington's Disease and Alzheimer's Disease (for a review, Tsai, G. and Coyle, J. T., *Prog. in Neurobiol.* 56:531–540 (1995)).

The incidence rate of TD increases throughout the patient's exposure to antipsychotic drugs. The longer the exposure, the higher the patient's risk of developing TD. This phenomenon points to the inadequacy of preclinical trials which only assess the risk of TD during the trial period. This phenomenon also suggests that the neuronal insults associated with TD are cumulative and the process which leads to this disease may be insidious and subtle in nature.

There is accumulating evidence suggesting that antipsychotics can induce oxidative stress through a variety of mechanisms. Elevated levels of conjugated dienes and thiobarbituric acid reactive products (TBARS) in the CSF of TD patients have been reported (Pall, H. S., et al., *Lancet* ii:596–599 (1987); Lohr, J. B., et al., *Biol. Psychial.* 28:535–539 (1990); Jeste, D. V., et al., *Psychopharmacology* 106:154–160 (1992)).

Elevated oxyradicals can inhibit presynaptic glutamate uptake, inactivate the enzymatic defenses against cellular oxidants (Volterra, A., et al, *J. Neuroscience* 14:2924–2932 (1994)) and disrupt mitochondrial electron transport (Burkhardt, C., et al., *Ann. Neurol.* 33:512–517 (1993); Jackson-Lewis, V. and Przedborski, S., *Ann. Neurol.* 35:244–245 (1994)), which results in an increased generation of superoxide and extraneuronal excitatory amino acids. Persistent activation of glutamate ionotropic receptors has long been known to cause neuronal degeneration (Olney, J. W., *Annu. Rev. Pharmacol. Toxicol.* 30:47–41 (1990)). Recent studies indicate that oxidative damage mediates the delayed neuronal degeneration caused by activation of N-methyl-D-aspartate (NMDA) and non-NMDA glutamate ionotropic receptors (Coyle, J. T. and Puttfarcken, P., *Science* 262:689–695 (1993)). This oxidative damage can be gradual, insidious and cumulative leading to an apoptotic form of neuronal death. It provides an important pathologic link between moderate levels of excessive glutamate ionotropic receptor stimulation and delayed neuronal degeneration.

The sources of oxyradicals produced as a consequence of long-term antipsychotic exposure are diverse and remain incompletely characterized. Depolarization activates oxidative metabolism of glucose via the mitochondrial electron transport chain with the superoxide radical generated as a byproduct. Recent reports indicate that antipsychotics inhibit the mitochondrial electron transport chain at Complex I, which would further enhance superoxide generation (Burkhardt, C., et al., *Ann. Neurol.* 33:512–517 (1993); Jackson-Lewis, V. and Przedborski, S., *Ann. Neurol.* 35:244–245 (1994)), and CSF metabolic abnormalities found in this cohort of patients is consistent with an impairment of mitochondrial electron transport at Complex I (Goff, D. C., et al., *Amer. J. Psychiat.* 152:1730–1736 (1995)). Another possibility, however, is that an increased turnover of catecholamines results in free-radical formation. Nevertheless, it is unclear whether antipsychotics can directly generate free radicals and a reliable screening method for the potential of antipsychotic-induced TD does not exist.

The hypothesis of oxidative damage to striatal neurons mediated by antipsychotic enhancement of glutamatergic neurotransmission is supported by recent reports that Vitamin E reverses the symptoms of TD. The anecdotal reports have been sustained by double blind placebo controlled studies with Vitamin E (Egan, M. F., et al., *Amer. J. Psychiat.* 149:773–777 (1992); Adler, L. A., et al., *Amer. J. Psychiat.* 150:1405–1407 (1993)). Notably, those patients earlier in the course of their disorder are more responsive to treatment with Vitamin E, consistent with the model that the oxidative damage is cumulative over time and involves functional impairment prior to frank degeneration. Similarly, in a double blind placebo controlled study of Vitamin E treatment of patients with Huntington's Disease, those who were less symptomatic at the initiation of treatment exhibited the most favorable response (Peyser, C. E., et al., *Amer. J. Psychiatry* 152:1771–1775 (1995)). Inasmuch as centrally active free radical scavengers may not only reverse the oxidative damage, additional studies on oxidative stress in TD as well as efficacy of prevention and treatment with centrally active free radical scavengers on the surrogates oxidative stress in TD need to be carried out.

One of the major sources of potential oxidative stress in the brain is redox active metals (reviewed in Markesbery, W. R., *Free Radic. Biol. Med.* 23: 134–147 (1997)). Iron and copper are highly concentrated in the basal ganglia. Reduction of iron (III) and copper (II) generates iron (II) and copper (I), respectively. In Wilson's disease, there is progressive accumulation of copper within the body tissues, particularly the erythrocytes, kidney, liver and brain. In the blood, more than 90% is found in the plasma associated with ceruloplasmin. Copper absorption appears to be accelerated, and although the urinary excretion of free copper is usually increased, affected individuals of Wilson's disease are in positive copper balance. In addition to Wilson's disease, abnormal copper metabolism exists in the neurodegenerative disorders of Menkes' syndrome and possibly familial amyotrophic lateral sclerosis. Caudate, putamen, cerebral cortex and the dentate nuclei are the vulnerable regions in Wilson's disease. When cerebral copper accumulation is sufficient to destroy the nerve cells, the neurological syndrome begins. The most common features of this disease include choreoathetoid movements, muscular rigidity, and tremor of the extremities which have remarkable similarity to the symptoms of TD.

Although the relevance of oxidative stress to TD is becoming clear, a rational neurochemical basis for developing antipsychotics devoid of TD is lacking. While Vitamin E treatment has been used with some success, drugs aiming at the source of oxidative stress in TD is missing. The application of other antioxidants will not address the underlying pathogenesis mechanism.

SUMMARY OF THE INVENTION

The present invention provides screening methods for identifying compounds which induce TD when administered to an animal. These methods involve contacting a candidate compound with one or more reducible substrates, assaying for the production of one or more reaction intermediates or products associated with the reduction of the reducible substrate(s), and comparing the production of reaction intermediate(s) or product(s) to a standard production of reaction intermediate(s) or product(s), the standard being determined using a standard reaction mixture which does not contain the candidate compound. The production of significant quantities of reaction intermediate(s) or product(s) over the standard indicates that the candidate compound induces TD when administered to an animal.

Aspects of the present invention include screening methods for identifying compounds which induce TD when administered to an animal, wherein the ability of the candidate compound to (a) reduce a reducible substrate from a first oxidation state to a second lower oxidation state or (b) engage in chemical reactions which result in the production of one or more free radicals, precursors or intermediates of free radicals, or reactive oxygen species is measured. As above, the ability of the candidate compound to reduce the reducible substrate or engage in the specified chemical reaction(s) is determined by comparison to a standard determined in the absence of candidate compound.

Preferred methods of the present invention comprise assays which measure the ability of a candidate compound to:

(a) reduce a reducible substrate (e.g., copper (II) or iron (III)) from a first oxidation state to a second lower oxidation state;

(b) engage in chemical reactions which result in the production of peroxides (e.g., hydrogen peroxide); or (c) engage in chemical reactions which result in the production of free radicals (e.g., hydroxyl radicals).

The present invention also provides methods employing combinations of more than one assay of the present invention, wherein a significant deviation from the standard reaction mixture in each of these assays confirms that the candidate compound induces TD when administered to an animal.

The present invention also provides combinations of one or more of the assays of the present invention and testing of the candidate compound in an animal model (e.g., a rodent model) to confirm that the candidate compound induces TD when administered to an animal.

The present invention further provides combinations of one or more of the assays of the present invention and testing of the candidate compound for additional activities (e.g., superoxide dismutase activity, catalase activity) to determine whether the candidate compound induces TD when administered to an animal.

The present invention also provides high-throughput assays for screening candidate compounds to identify those compounds which induce TD when administered to an animal.

The present invention further provides methods for treating psychoses comprising the testing of candidate compounds to identify those which will not induce tardive dyskinesia when administered to an animal, and administering one or more of these compounds to a patient in need thereof.

DETAILED DESCRIPTION

Definitions

Figure 1:
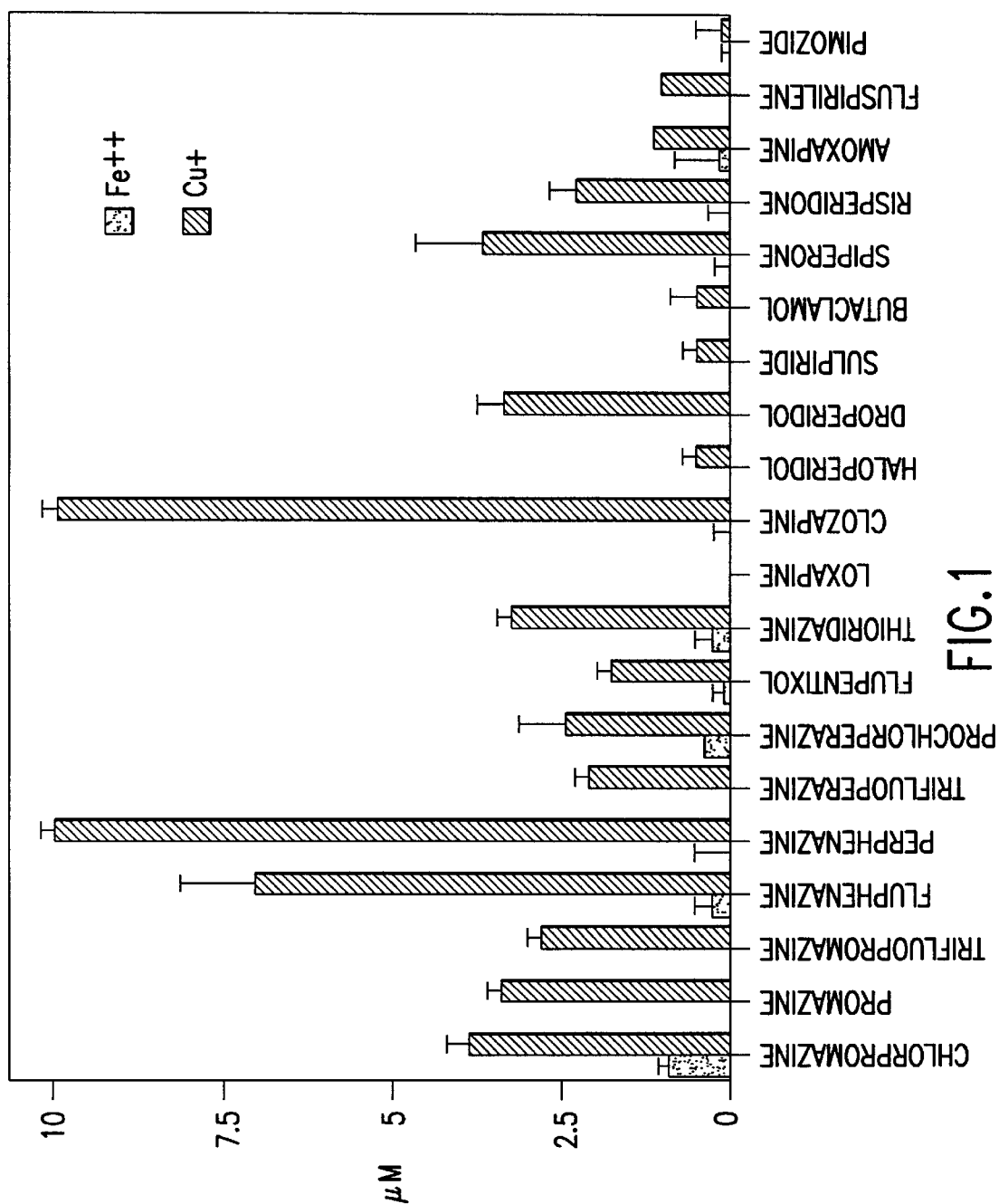
FIG. 1 shows the results of copper and iron reduction assay for various antipsychotic drugs. The data were generated using the methods disclosed in Example 1(a).

The following definitions are provided to clarify the subject matter which the inventors consider to be the present invention.

As used herein, the phrase "candidate compound" refers to both antipsychotic drugs and compounds potentially useful as antipsychotic drugs which are screened by the methods of the present invention to determine whether these compounds induce TD. The term "compound" includes synthetic molecules and naturally occurring products, whether present in purified form or crude mixture.

As used herein, the term "animal" refers to members of the animal kingdom. Preferred animals are mammals. Most preferred animals are humans.

As used herein, the phrase "reactive oxygen species" refers to molecules (and singlet oxygen) which contain oxygen and are generally either toxic to biological systems or readily engage inreactions which produce toxic by-products. Reactive oxygen species include superoxide anions ($O_2^{\cdot-}$), hydroxyl radicals ($OH^{108}$), and hydrogen peroxide ($H_2O_2$). These reactive oxygen species do not include molecular oxygen ($O_2$).

As used herein, the phrase "reducible substrate" refers to an element or complex ion which can be reduced in a redox reaction. The standard reduction potential of the redox reaction for reducible substrates useful in the practice of the present invention will generally be below 2.0 E°/V.

As used herein, the phrase "complex ion" refers to an ion which is not an element. Examples of complex ions include compounds such as $Mn(OH)_3$, $Pt(OH)_2$, and proteins. Proteins are considered to be complex ions, even if they do not have a net positive or negative charge, as long as they have regions which can participate in redox reactions.

As used herein, the phrase "standard reaction mixture" refers to a control reaction mixture which contains all of the ingredients of a reaction mixture used to assay for determining whether a candidate compound can induce TD except for the candidate compound. This mixture may be assayed before, at the same time, or after the reaction mixture containing the candidate compound. The standard reaction mixture is also referred to herein as a "blank".

As used herein, the phrase "tardive dyskinesia", abbreviated "TD", refers to an affliction characterized by involuntary movement of muscles resulting from neuronal degeneration induced by antipsychotic drugs.

As used herein, the term "antipsychotic" and the phrase "antipsychotic drug" refer to psychotropic drugs used in the treatment of psychoses. For purposes herein, the terms "antipsychotic" and "neuroleptic" are equivalents.

As used herein, the term "psychosis" (plural being "psychoses") refers to a mental disorder which causes gross disorganization of a person's mental capacity to recognize reality and to communicate and relate to others to the degree that the disorder interferes with the afflicted person's ability to cope with the occurrences of everyday life.

Additional definitions are provided throughout the specification.

Screening Methods of the Present Invention

We have found the cerebrospinal fluids of TD patients have lower SOD activity and higher levels of protein carbonyl groups than TD-free subjects. SOD is an enzyme critical in the detoxification of superoxide, a byproduct of oxidative metabolism. These results suggest that attenuated activity of SOD may contribute to increased oxidation of protein. Chronic treatment of rats with fluphenazine has been reported to cause a decrease in SOD and catalase activities in the nervous system. Decreased SOD renders neurons more vulnerable to oxyradical injury, consistent with the elevated levels of protein carbonyl groups. While we did not observe an elevation in lipid hydroperoxides in CSF in TD, elevated levels of conjugated dienes and thiobarbituric acid reactive products (TBARS) in the CSF of TD patients have been reported. These findings are consistent with the final results of oxidative damage. Nevertheless, the pathophysiological basis of antipsychotic-induced oxidative stress in unclear.

Figure 11:
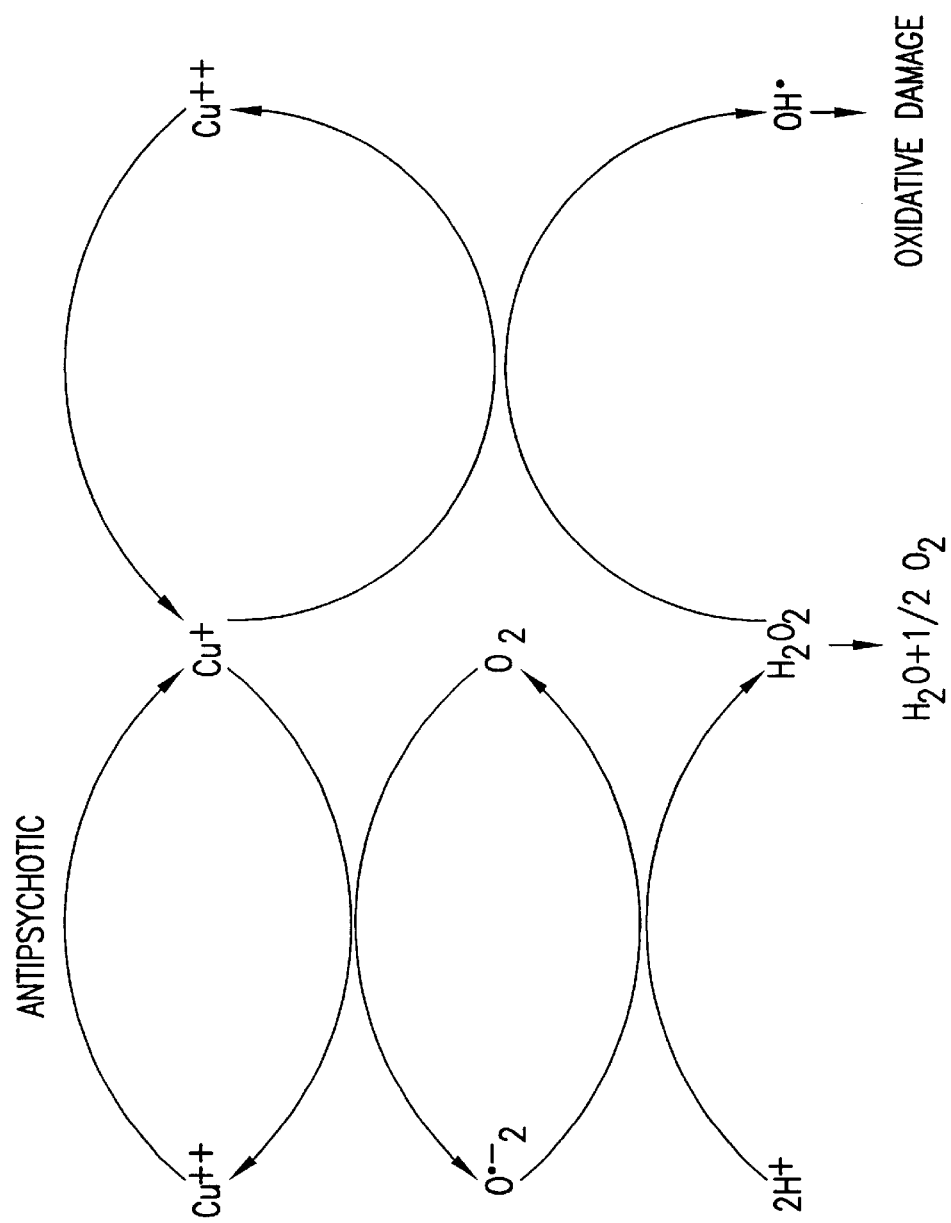
FIG. 11 shows the redox reactions predicted to occur in vivo when antipsychotic drugs which induce TD are administered to an animal.

The purpose of the present invention is to investigate the underlying pathophysiological mechanism of TD, which we hypothesize is a cumulative process, and provide an in vitro tool for determining the potential of antipsychotics to induce TD in vivo. Thus, the present invention provides a facile tool for the screening of candidate compounds, such as candidate antipsychotic drugs, which predict the compound's likelihood of inducing TD when administered to an animal. This is based upon our discoveries relating to the underlying pathophysiological mechanism of TD, which we hypothesize is due to an oxidative stress-related cumulative process caused by the redox chemistry of the antipsychotic drugs themselves. As shown in FIG. 11, antipsychotic drugs are believed to induce TD when administered to an animal as a result of their ability to convert Cu(II) to Cu(I). This ability to reduce copper ions in vivo is thought to result in the formation of reactive oxygen species which induce neuronal oxidative damage. (FIG. 11.)

Metal ions are believed to engage in reactions which result in the production of reactive oxygen species in biological organisms (reviewed in Markesbery, W. R., *Free Radic. Biol. Med.* 23:134–147 (1997)). One series of such reactions, shown below, concludes with the Fenton reaction, shown in (c), and the formation of hydroxyl radicals.

(a) Reduced Compound+$O_2$→Oxidized Compound+$O_2^{\cdot-}$ (e.g., $Fe^{2+}$, $Cu^{1+}$) (e.g., $Fe^{3+}$, $Cu^{2+}$)

(b) $O_2^{\cdot-}+O_2^{\cdot-}+2H^+$→$H_2O_2+O_2$ (c) Reduced Compound+$H_2O_2$→Oxidized Compound+ $OH^{\cdot}+OH^-$(e.g., $Fe^{2+}$, $Cu^{1+}$) (e.g., $Fe^{3+}$, $Cu^{2+}$)

Figure 9:
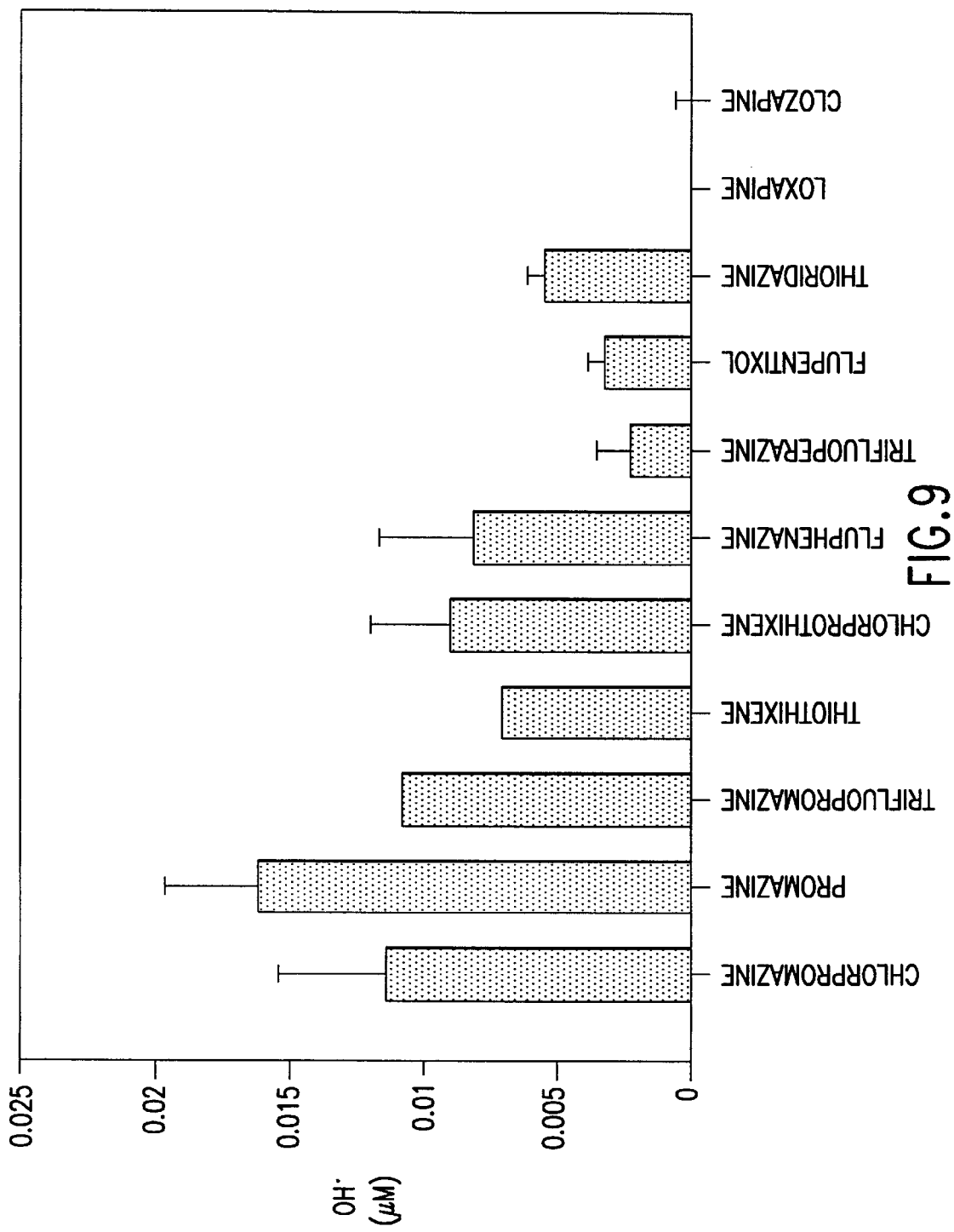
FIG. 9 shows the production of hydroxyl radical by antipsychotics. The data were generated using the methods disclosed in Example 1(c).

As shown in FIG. 9, most of the antipsychotics currently in use and known to cause TD generate the hydroxyl radical (OH⁻) by Fenton chemistry. Like Aβ amyloid, these antipsychotics have the capacity to reduce Cu(II) to Cu(I), and form hydrogen peroxide ($H_2O_2$) (FIGS. 1 and 3, respectively) from the apparently spontaneous reduction of molecular oxygen to superoxide, simultaneously. The reduced Cu(I) and $H_2O_2$ react to generate the hydroxyl radical. No other class of drug or psychotropic is capable of generating OH. in this manner, and clozapine, the only antipsychotic with a low potential for inducing TD as an adverse effect, is also unable to generate OH.

Clozapine presents an exception to the correlation between copper reduction activity and the ability to induce TD by antipsychotic drugs. As shown in FIG. 1, clozapine has potent copper reduction activity which suggests that this drug induces TD when administered to an animal. Our data indicates, however, that this drug may exhibit superoxide dismutase and catalase activities which apparently scavenge hydroxyl radical precursors. This conclusion is supported by the fact that, as shown in FIG. 9, clozapine does not generate significant amounts of hydroxyl radicals.

We have adapted this system into a rapid through means for determining which compounds generate OH. and therefore predicting which compounds would be candidates for causing TD. Our invention provides a systemic appraisal of the TD-inducing risk of antipsychotics. From our invention, antipsychotic drugs can be identified which should not be capable of either reducing Cu(II) or generating reactive oxygen species in vivo upon administration to an animal. Thus, the present invention further allows for the identification of compounds which will not induce TD when administered to an animal. Such compounds may be identified, for example, by their inability to reduce a reducible substrate or engage in chemical reactions which result in the production of free radicals, precursors of free radicals, or reactive oxygen species in vitro.

The present invention can be practiced using virtually any method wherein the ability of a candidate compound to reduce a reducible substrate from a first oxidation state to a second lower oxidation state or engage in chemical reactions which result in the production of free radicals, precursors of free radicals, or reactive oxygen species is measured.

In each embodiment of the invention, the data obtained in the presence of the candidate compound is compared to a standard reaction mixture which is essentially identical to that containing the candidate compound except the candidate compound is absent. This standard reaction mixture may be assayed at the same time as the reaction mixture containing the candidate compound or may be assayed prior or subsequent to the mixture containing the candidate compound.

As noted above, the screening methods of the present invention are based on the redox chemistry of the candidate compound itself which is believed to be responsible for the induction of TD. Thus the present invention encompasses any assay method which identifies characteristics of candidate compounds which result in the induction of TD when administered to an animal. As shown in FIG. 1, one characteristic of compounds which induce TD is the ability to reduce Cu(II) to Cu(I). As also shown in FIG. 1, these compounds also have some Fe(III) reduction activity. The ability of antipsychotic drugs to reduce Cu(II) more readily than Fe(III) is believed to be related to the standard reduction potentials of each ion. As shown in Table 1, the standard reduction potential for the conversion of Cu(II) to Cu(I) (0.153 E°/V) is much lower than for the conversion of Fe(III) to Fe(II) (0.771 E°/V). Thus, the present invention encompasses methods for identifying compounds capable of reducing ions with standard reduction potentials between 0 and 2.0 E°/V, more preferably between 0 and 1.6, 0 and 0.8, 0 and 0.6, or 0 and 0.4 E°/V and most preferably between 0 and 0.2 E°/V.

TABLE 1

Representative Examples of Standard Reduction Potentials.*

| Reaction | E°/V |
| --- | --- |
| $Mn(OH)_3 + e \leftrightarrow Mn(OH)_2 + OH^-$ | 0.15 |
| $Cu^{2+} \leftrightarrow Cu^+$ | 0.153 |
| $BiCl_4^- + 3e \leftrightarrow Bi + 4 Cl^-$ | 0.16 |
| $Fe^{3+} \leftrightarrow Fe^{2+}$ | 0.771 |
| $Mn^{3+} \leftrightarrow Mn^{2+}$ | 1.5415 |

*An extensive list of standard reduction potentials is provided in the CRC HANDBOOK OF CHEMISTRY AND PHYSICS, 72nd Edition, CRC Press (1992), pages 8–17 to 8–29.

The standard reduction potentials of several ions are shown in Table 1. Since, as noted above, the induction of TD by antipsychotic drugs is linked to the compounds redox chemistry, one skilled in the art could readily identify reducible substrates potentially suitable for use in the practice of the present invention. For example, as shown in Table 1, the standard reduction potential for the conversion of Cu(II) to Cu(I) (0.153 E°/V) is significantly lower that for the conversion of Fe(III) to Fe(II) (0.771 E°/V) and Cu(II) is more readily reduced than Fe(III) (FIG. 1). By using suitable assays, the inventors believe that candidate compound induced reduction of reducible substrates having standard reduction potentials as high as 2.0 E°/V may be quantified.

The present invention also encompass assays which measure the reduction of both biological molecules and complex ions by a candidate compound. Drugs have been reported to engage in redox reactions with both complex ions and proteins. Ferric bleomycin, for example, has been reported to catalyze the reduction of 10-hydroperoxy-8,12- octadecadienoic acid in vitro. Padbury, G. et al., *Biochem.* 27:7846–7852 (1988). Similarly, dopamine has been shown to undergo oxidation in the presence of L-cysteine. Shen, X. M. et al., *Chem. Res. Toxicol.* 10:147–155 (1997). Further, beta-adrenergic receptor blocking medications are believed to oxidize proteins in vivo. Lamont, S., *J. Cardpulm. Rehabil.* 15:183–185 (1995).

A considerable number of assays are known in the art for measuring redox reactions. For example, redox titrations may be used to identify and quantify ionic species produced via redox reactions. One example of such a titration involves the use of $KMnO_4$ which becomes colorless upon oxidizing Fe(II) to Fe(III). When all of the Fe(II) in a sample has been converted to Fe(III), the titrated sample will retain the purple color of the titration reagent. Brady, J. E. and Holum, J. R., *FUNDAMENTALS OF CHEMISTRY*, John Wiley and Sons, 1984, pages 392–396. Similar titration assays are also available for quantifying copper ion species. See, e.g., J. E. Brady and J. R. Holum, supra.

The present invention further encompasses methods for screening candidate compounds to identify those which induce TD by measuring the production of one or more intermediates or products of reactions associated with the reduction of reducible substrate or with the induction of TD by antipsychotic drugs. These methods include, in addition to redox assays, assays for detecting superoxide anions, hydrogen peroxide, and hydroxyl radicals generated by antipsychotic drugs.

By the phrase "intermediates or products of reactions associated with the reduction of reducible substrate" is meant intermediates and end product directly or indirectly formed by reactions which occur as a result of the reduction of reducible substrate (e.g, Fenton reaction products, hydrogen peroxide, superoxide anion).

A considerable number of assays are known for measuring both the concentrations and production of the reactants and products shown in FIG. 11. Assays for detecting and quantifying superoxide anions as well as other reactive oxygen species (e.g., $H_2O_2$ and $OH^-$), for example, are known in the art. See, e.g., Lemaire, P. and Livingston, D. R., *Comp. Biochem. Physiol. C. Pharmacol. Toxic. Endocrinol.* 11 7:131–139 (1997); Kelm, M. el al., *J. Biol. Chem.* 272:9922–9932 (1997); Masuoka, N. et al., *Clin. Chim. Acta.* 254:101–112 (1996); Zeller, J. M. and Sullivan, B. L., *J. Leukoc. Biol.* 52:449–455 (1992). Such assays may be based on a variety of different detection mechanisms including colorimetric detection (Lavoie, J. C. and Chessex, P., *J. Pediatr. Gastroenterol. Nutr.* 25:307–311 (1997)), the use of chemiluminescent (Kojima, S. et al., *Anticancer Res.* 14:1875–1880 (1995)) or fluorescent probes (Biaglow, J. E. and Kachur, A. V., *Radial. Res.* 148:181–187 (1997)), and electron spin resonance spectroscopy (Lee, C. and Okabe, E., *Jpn. J. Pharmacol.* 67:21–28 (1995)).

Figure 3:
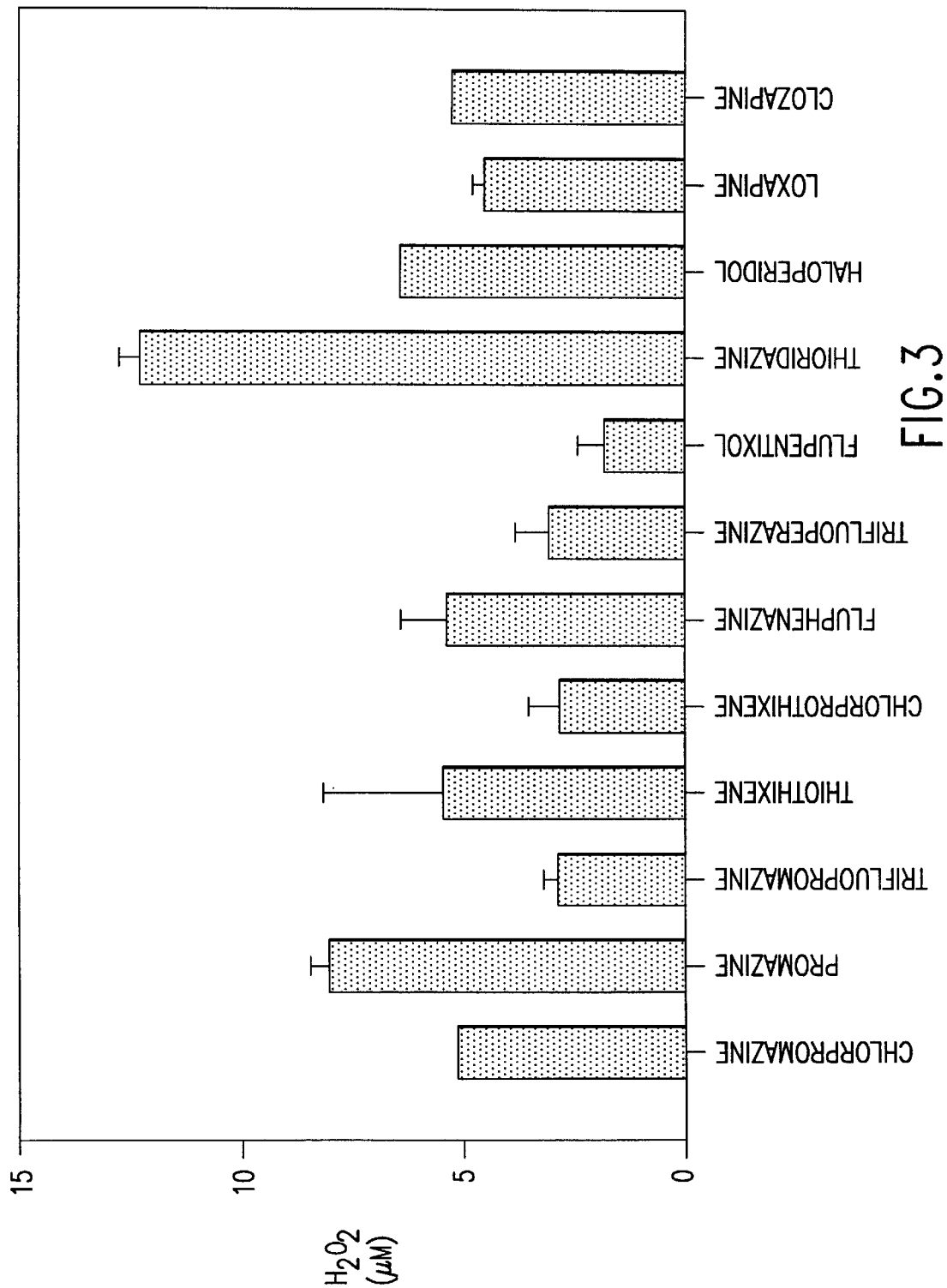
FIG. 3 shows the results of hydrogen peroxide production assays for various antipsychotic drugs. The data were generated using the methods disclosed in Example 1(b).
Figure 4:
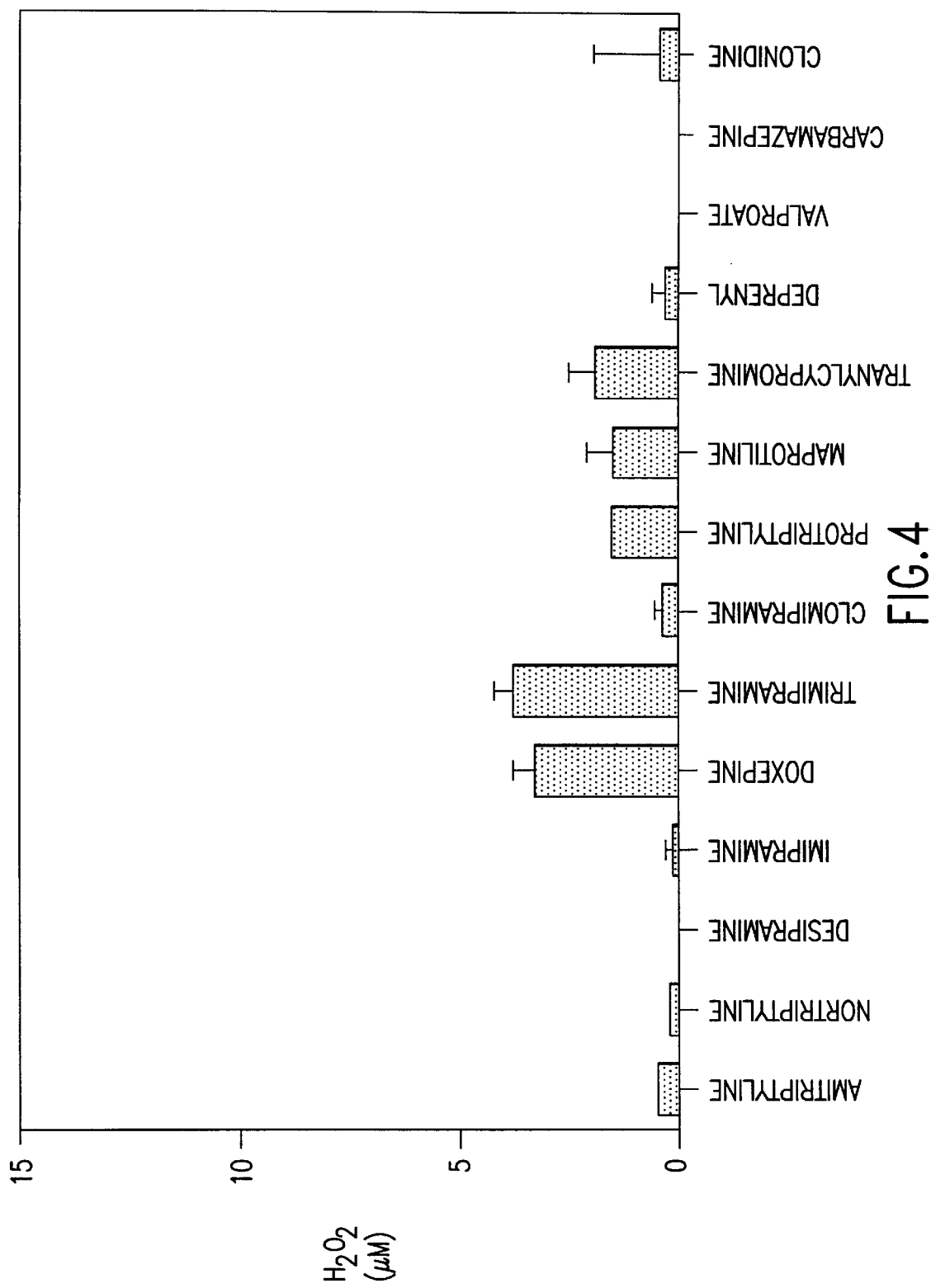
FIG. 4 shows the results of hydrogen peroxide production assays for various non-antipsychotics. The data were generated using the methods disclosed in Example 1(b).
Figure 5:
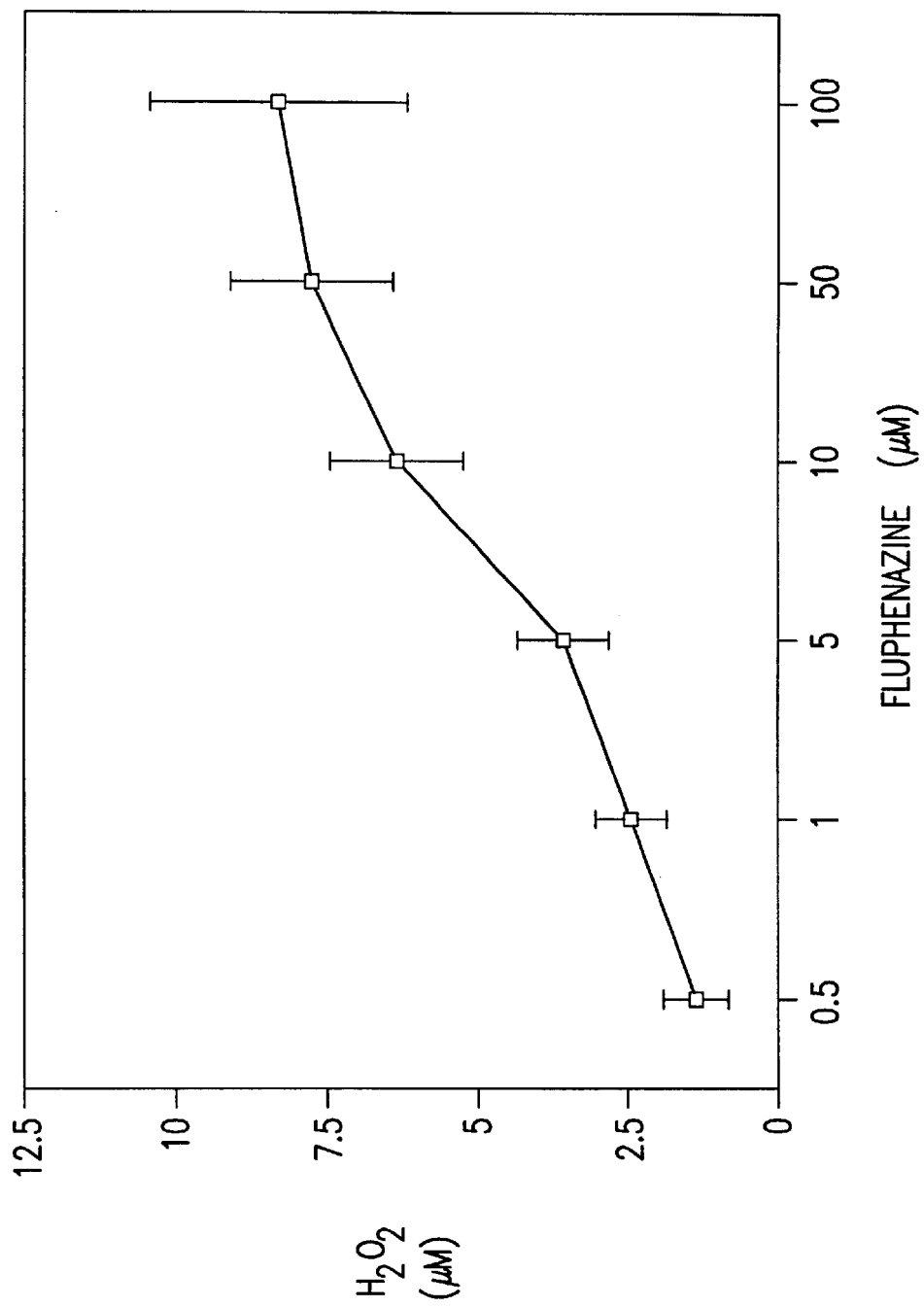
FIG. 5 shows the dose response of the generation of hydrogen peroxide by fluphenazine. The data were generated using the methods disclosed in Example 1(b).

One embodiment of the present invention is shown in Example 1(b) where candidate compounds were tested for the ability to generate hydrogen peroxide in the presence of Cu(II). (FIGS. 3–5.) The present invention encompasses variations of the method disclosed in Example 1(b) where a reducible substrate is contacted with a candidate compound and the generation of hydrogen peroxide is measured.

A second embodiment of the present invention is shown in Example 1(c) where candidate compounds were tested for the ability to generate hydroxyl radicals in the presence of Cu(II). The present invention encompasses variations of the method disclosed in Example 1(c) where a reducible substrate is contacted with a candidate compound and the generation of hydroxyl radicals is measured.

As one skilled in the art would appreciate, once a candidate compound has been identified by an assay of the present invention as one which does not induce TD, additional testing may be required to confirm this finding. A number of methods are available for confirming that the candidate compound does not induce TD when administered to an animal. For example, multiple assays of the present invention may be performed using the same candidate compound, after which, the data generated is used to predict whether the candidate compound will induce TD when administered to an animal. For instance, a candidate compound which has reduction activity towards a reducible substrate but does not generate hydroxyl radicals would not be predicted to induce TD.

The prediction that a candidate compound does not induce TD when administered to an animal can also be tested by assaying additional characteristics of the compound. For example, a candidate compound which has reduction activity towards a reducible substrate, and has one or more activities which eliminate reactive oxygen species would not be expected to induce TD when administered to an animal. The antipsychotic drug clozapine is such a compound and does not induce TD when administered to an animal. As noted above, the inventors have found that clozapine may possess both superoxide dismutase and catalase activities which would eliminate hydroxyl radical precursors prior to the formation of significant quantities of these radicals.

Figure 12:
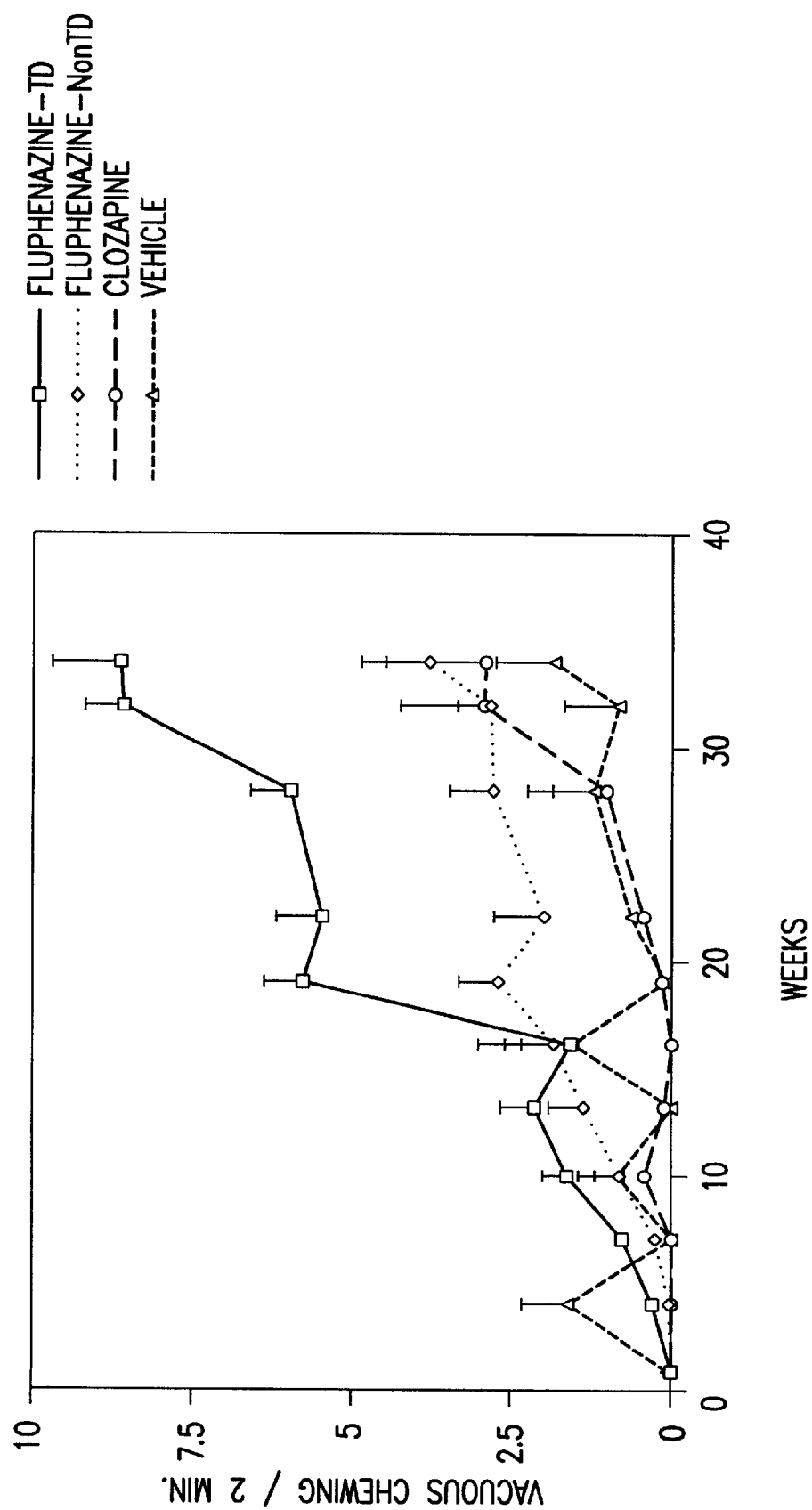
FIG. 12 shows vacuous chewing movement in rats during a 36 week time course treated with fluphenazine (TD and non-TD groups), clozapine and vehicle for the first 24 weeks and withdrawn for the final 12 weeks.

Confirmation of the prediction that a candidate compound does not induce TD when administered to an animal can also be made using animal models. There are two major animal models of TD. The first is a primate model of antipsychotic-induced dyskinesia. Ten to thirty percents of Cebus or Maccaca monkeys will develop clinical dyskinesia after long-term antipsychotic treatment. The second is a rodent model of vacuous chewing. In the rodent model, when the animals are treated with antipsychotics, they develop vacuous chewing, which has phenomenological similarities to the orobuccofacial movement of TD. Only 30–60% of rats will develop vacuous chewing. The chewing movement is enhanced after the withdrawal of antipsychotic treatment. Similar to the clinical situation, clozapine and vehicle treatment only induce vacuous chewing in a small portion of the animals. (FIG. 12.)

Animals which receive antipsychotic drugs and develop dyskinesia have higher levels of reduced copper, hydrogen peroxide and hydroxy radical generation in the movement-related brain regions, such as striatum. In vivo dialysis techniques can be applied to detect the changes in redox active metals, as well as hydrogen peroxide and hydroxy radical generation. TD can be prevented or treated in the animals used in this model by the chelation of copper and antioxidant administration.

Many of the assays useful in the practice of the present invention are readily adaptable for use in high-throughput assays for screening candidate compounds to identify those which induce TD when administered to an animal. To achieve high-throughput screening, it is best to house samples on a multicontainer carrier or platform. A multicontainer carrier facilitates measuring reactions of a plurality of candidate compounds simultaneously. In one embodiment, a multi-well microplate, for example a 96 or a 384 well microplate, which can accommodate 96 or 384 different test reactions, is used as the carrier. Such multi-well microplates, and methods for their use in numerous assays, are both known in the art and commercially available. Sigma Chemical Co., BIOCHEMICAL ORGANIC COMPOUND AND DIAGNOSTIC REAGENTS, 1996 Catalog, pages 2134, 2483–2497.

In one embodiment, reactants are contained in each well of a multi-well microplate. The standard well(s) contains all of the reactants except the candidate compound. Each of the non-standard wells contain at least one candidate compound. The reaction measured in the non-standard wells are generally each compared against the reaction measured in the standard well(s).

Techniques for measuring the progression of reactions in multicontainer carrier facilitates are known in the art and include spectrophotometry and spectrofluorometry. Colorimetric assays for measuring the concentrations of chemical reactants are well known in the art. Examples of such assays are included in Example 1(a) and include the use of bathocuproine disulfonate (BC) and bathophenanthroline disulfonate (BP) to measure the concentration of Cu(I) and Fe(II) ions, respectively. Further examples of such assays include the use of colorimetric assays for the detection of peroxides, as disclosed in Example 1(b) and Gordon, A. J. and Ford, R. A., THE CHEMIST'S COMPANION: A HANDBOOK OF PRACTICAL DATA, TECHNIQUES, AND REFERENCES, John Wiley and Sons, N.Y., 1972, Page 437.

In one embodiment fluorescence spectrometry is used to monitor the generation of reaction products. Fluorescence methodology is generally more sensitive than the absorption methodology. The use of fluorescent probes is well known to those skilled in the art. Reviewed in Bashford, C. L. et al., SPECTROPHOTOMETRY AND SPECTROFLUOROMETRY: A PRACTICAL APPROACH, pp. 91–114, IRL Press Ltd. (1987); Bell, J. E., SPECTROSCOPY IN BIOCHEMISTRY, Vol. I, pp. 155–194, CRC Press (1981). One method readily adaptable for use in high-throughput assays employs a fluorescent probe, coumarin-3-carboxylic acid, for the detection of hydroxyl radicals. Biaglow, J. E. and Kachur, A. V., Radiat. Res. 148:181–187(1997).

Spectral readings can be taken on all of the samples housed in a multicontainer carrier simultaneously. Alternatively, readings can be taken on samples in groups of at least two at a time or one sample at a time. Further, the standard well(s) may be read at the same time as each non-standard well or the standard well(s) may be read prior or subsequent to the reading of each non-standard well. The choice of when to read the samples containing the candidate compounds and the standard reaction mixture(s) will often vary with numerous factors including whether the reaction being assayed is continuously progressing or has either reached an end point or has been "stopped" by other means (e.g., via an alteration in pH or the addition of a chelating agent).

The present invention also provides methods for treating psychoses comprising the testing of candidate compounds to identify compounds which will not induce tardive dyskinesia when administered to an animal, and administering one or more such compounds to a patient in need thereof.

The antipsychotic drug(s) which will not induce TD is administered to a patient as part of a pharmaceutical mixture at levels sufficient to treat psychoses. The amount of the antipsychotic drug administered to the patient will be formulated in accordance with medical practice and will vary with such factors as the patient's condition and the drug being administered.

The antipsychotic drug may be administered by any route that delivers efficacious levels of the drug, e.g., orally, intranasally, parenterally. For parenteral administration, preparations containing the antipsychotic drug may be provided to a patient in need of such treatment in combination with pharmaceutically acceptable sterile aqueous or non-aqueous solvents, suspensions and emulsions. Examples of non-aqueous solvents are propylene glycol, polyethylene glycol, vegetable oil, and injectable organic esters. Aqueous carriers include water, water-alcohol solutions, Ringer's dextrose solution, dextrose plus sodium chloride solution, Ringer's solution containing lactose, or fixed oils.

Additional information related to dosages and the administration of drugs can be found in numerous sources including REMINGTON'S PHARMACEUTICAL SCIENCES, 18th Edition, 1990, Mack Publishing Co, Easton, Pa.

Having generally described the invention, the same will be more readily understood by reference to the following examples, which are provided by way of illustration and are not intended as limiting. Examples 1(a) through 1(c), below, provide assays useful in the practice of the present invention.

EXAMPLES

Example 1
Screening Assays for Determining Whether Antipsychotics Induce Tardive Dyskinesia Three separate assays for determining whether candidate antipsychotic drugs induce TD when administered to animals are provided in this example.

Example 1(a)
Reduction of Copper by Antipsychotics

For the purpose of studying the ability of antipsychotics to reduce Cu(II) and Fe(III) under different conditions, we devised a novel high-throughput assay, based upon a modification of published protocols (Landers, J. W. and Zak, B., Clin. Chim. Acta. 3:328 (1958); Landers, J. W. and Zak, B., Amer. J. Clin. Path. 29:590–592 (1958); Sayre, L. M. and Multhaup, G., Science 274:1933–1934 (1996)), to operate in a 96-well format.

Method: To test whether antipsychotics possess metal reducing properties, 10 $\mu$M of antipsychotics were co-incubated with 10 $\mu$M of Cu(II) and Fe(III) in PBS (pH 7.4) at 37° C. for 1 hour. The Cu(I) and Fe(II) indicators, bathocuproine disulfonate (BC) and bathophenanthroline disulfonate (BP), respectively, were present at 200 $\mu$M during the incubation, and the formation of Cu(I)-BC and Fe(II)-BP complexes were monitored at their absorption maxima: 483 nm and 536 nm, respectively, and concentrations calculated by comparison against standard curves. The blanks were the metal solutions in PBS with their indicators without the addition of antipsychotics. Therefore, the net production of reduced metals by antipsychotics can be calculated based on the absorbance difference between samples and blanks. The results indicate that antipsychotics reduce Cu(II) more readily than Fe(III) (FIG. 1). Since the standard reduction potential for Cu(II)/Cu(I) is much lower than Fe (III)/Fe(II), this result implies that reduction of Cu(II) may be specifically favored by antipsychotics. Hence, antipsychotics can produce highly reactive copper ion intermediates.

Example 1(b)
Generation of Hydrogen Peroxide by Antipsychotics

To determine whether antipsychotics themselves could be the source of peroxidation in TD, we measured hydrogen peroxide formation in vitro using a novel 96-well assay developed specifically for that purpose. The production of hydrogen peroxide is assayed by a modification of a published method (Han, J. C. and Han, G. Y., Anal. Biochem. 220:5–10 (1994); Han, J., et al., Anal. Biochem. 234:107–109 (1996)). We found that antipsychotics generate hydrogen peroxide in a copper-dependent manner. Antipsychotics (10 $\mu$M) were assayed for hydrogen peroxide formation in PBS (pH 7.4) in the presence of 10 $\mu$M Cu(II). Approximately 5–15 $\mu$M hydrogen peroxide was formed by antipsychotics in one hour (FIG. 3). This signal (as with all hydrogen peroxide signals generated in these studies) was abolished by the presence of catalase (100 U/ml), which rapidly removes hydrogen peroxide, confirming the validity of the assay.

Method: All buffers were treated with Chelex®-100 to remove as much trace metal contamination as possible, however this technique cannot remove metals to below the sub-picomolar level required to guarantee an environment that abolishes spontaneous dismutation, hence the presence of a chelator is necessary to achieve such a baseline. Ten $\mu$M of antipsychotics and 10 $\mu$M of Cu(II) were co-incubated with 100 $\mu$M of a $H_2O_2$-trapping reagent, Tris(2-Carboxyethyl)-Phosphine Hydrochloride (TCEP), in PBS (pH 7.4) at 37 ° C. for 1 hour. Then 100 $\mu$M of the detection reagent, 5,5'-Dithio-bis(2-Nitrobenzoic Acid) (DTNB), was added to react with the remaining TCEP, the reaction product possessing a characteristic absorbance maximum at 412 nm. We adapted the hydrogen peroxide assay (Han, J., et al., Anal. Biochem. 234:107–109 (1996)) for the rapid throughput study of antipsychotics by introducing a 96-well format, and by introducing a standard range of absorbance allowing us to empirically quantify hydrogen peroxide with a lower limit of detection of 0.5 $\mu$M.

Example 1(c)
Generation of Hydroxyl Radical by Antipsyclotics

To determine whether antipsychotics themselves could be the source of free radical generation in TD, we measured hydroxyl radical formation in vitro using a novel 96-well assay developed specifically for that purpose. The method used to assay hydroxy radical is a modification of a published method (Gutteridge, J. M. C. and Wilkins, S., Biochim. Biophys. Acta 759:38–41 (1983)). Antipsychotics (10 $\mu$M) were assayed for hydroxyl radical formation based on the evidence that hydroxyl radical is capable of degrading deoxyribose (DOR) with the formation of thiobarbituric acid-reactive products. We found that antipsychotics generate hydroxyl radical in a copper-dependent manner (FIG. 9).

Method: One $\mu$l of Cu(II) was added to 125 $\mu$l of 7.5 mM DOR and 10 $\mu$l of 1 $\mu$M individual antipsychotic and made up to 500 $\mu$l with PBS (pH 7.4) in a 1 ml tube. The reaction was incubated for 1 hour at 37° C. After incubation, 250 $\mu$l glacial acetic acid and 250 $\mu$l of thiobarbituric acid (1% w/v in 0.05 M NaOH) was added to the tubes which were then incubated at 100° C. for 15–20 minutes. The absorbance was read at 532 nm. We adapted the hydrogen peroxide assay for the rapid throughput study of antipsychotics by introducing a 96-well format (Han, J. C. and Han, G. Y., Anal. Biochem. 220:5–10 (1994); Han, J., et al., Anal. Biochem. 234:107–109 (1996)).

Results
Reduction of metals

Figure 2:
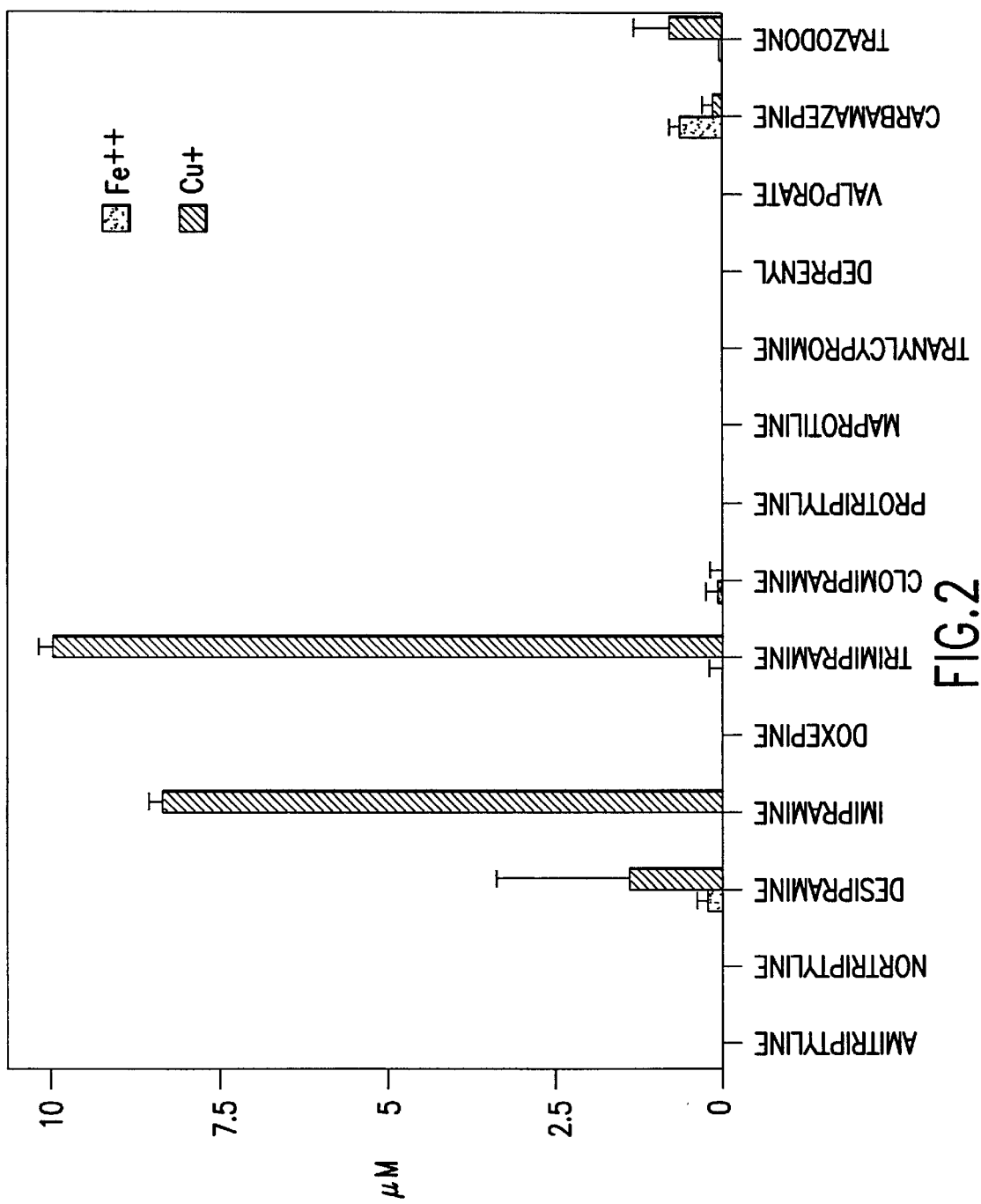
FIG. 2 shows the results of copper and iron reduction assays for various non-antipsychotic psychotropic drugs. The data were generated using the methods disclosed in Example 1(a).

We found that conventional antipsychotics selectively reduce copper and, to a much less degree, iron. (FIG. 1.) On the other hand, while a few of the non-antipsychotic psychotropic drugs tested will reduce copper ions, most will not reduce significant quantities of either Cu(II) or Fe(III). (FIG. 2.)

Generation of hydrogen peroxide

Antipsychotics also generate hydrogen peroxide in addition to their capacity to reduce metals. (FIG. 3.) On the other hand, many non-antipsychotic psychotropics do not generate appreciable quantities of hydrogen peroxide and those which do generate significantly less hydrogen peroxide than most of the antipsychotics drugs tested. (FIG. 4.)

Figure 6:
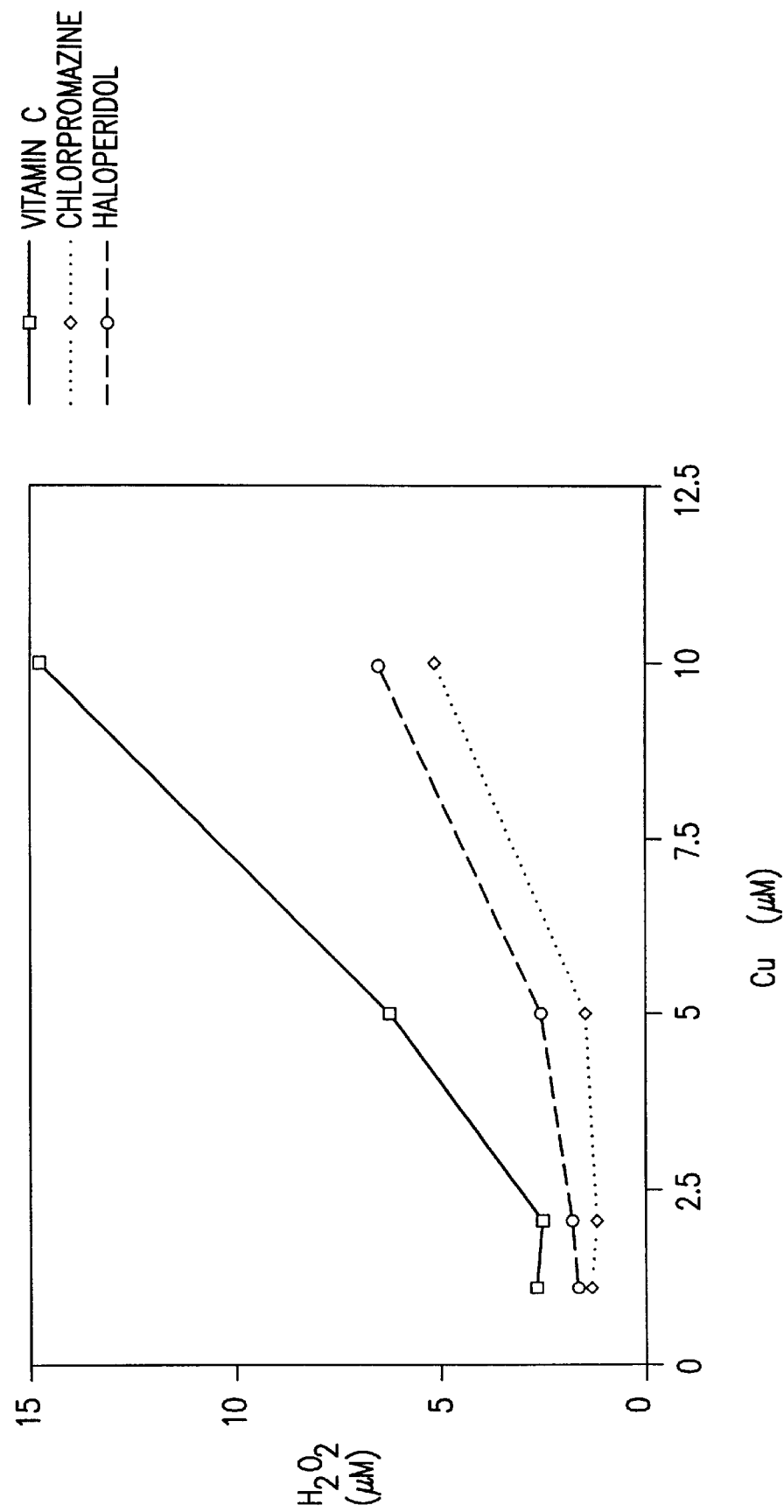
FIG. 6 shows the relationship between copper concentration and the generation of hydrogen peroxide production by Vitamin C and the antipsychotic drugs chlorpromazine and haloperidol The data were generated using the methods disclosed in Example 1(b).
Figure 7:
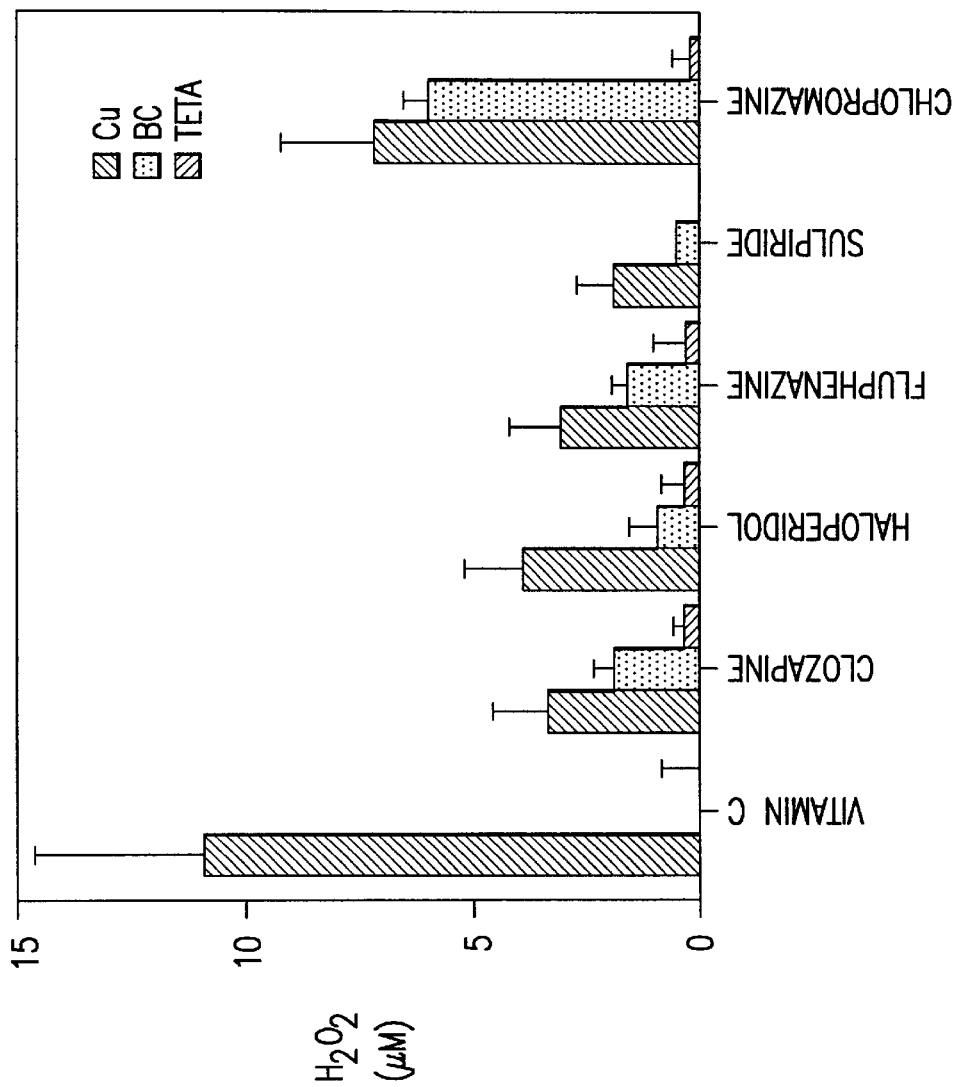
FIG. 7 shows that the chelating agents bathocuproine disulfonate (BC) and triethylenetetramine (TETA) significantly attenuate the production of hydrogen peroxide by Vitamin C and antipsychotics. The data were generated using the methods disclosed in Example 1(b).

The capacity of the antipsychotic fluphenazine to generate hydrogen peroxide is concentration dependent, i.e. more fluphenazine generates more hydrogen peroxide. (FIG. 5.) The capacity of this antipsychotic to generate hydrogen peroxide is also dependent on the concentration of copper, i.e. more copper generates more hydrogen peroxide when reacted with antipsychotics. (FIG. 6.) When copper is chelated, the capacity of antipsychotics to generate hydrogen peroxide is significantly attenuated. (FIG. 7.)

Figure 8:
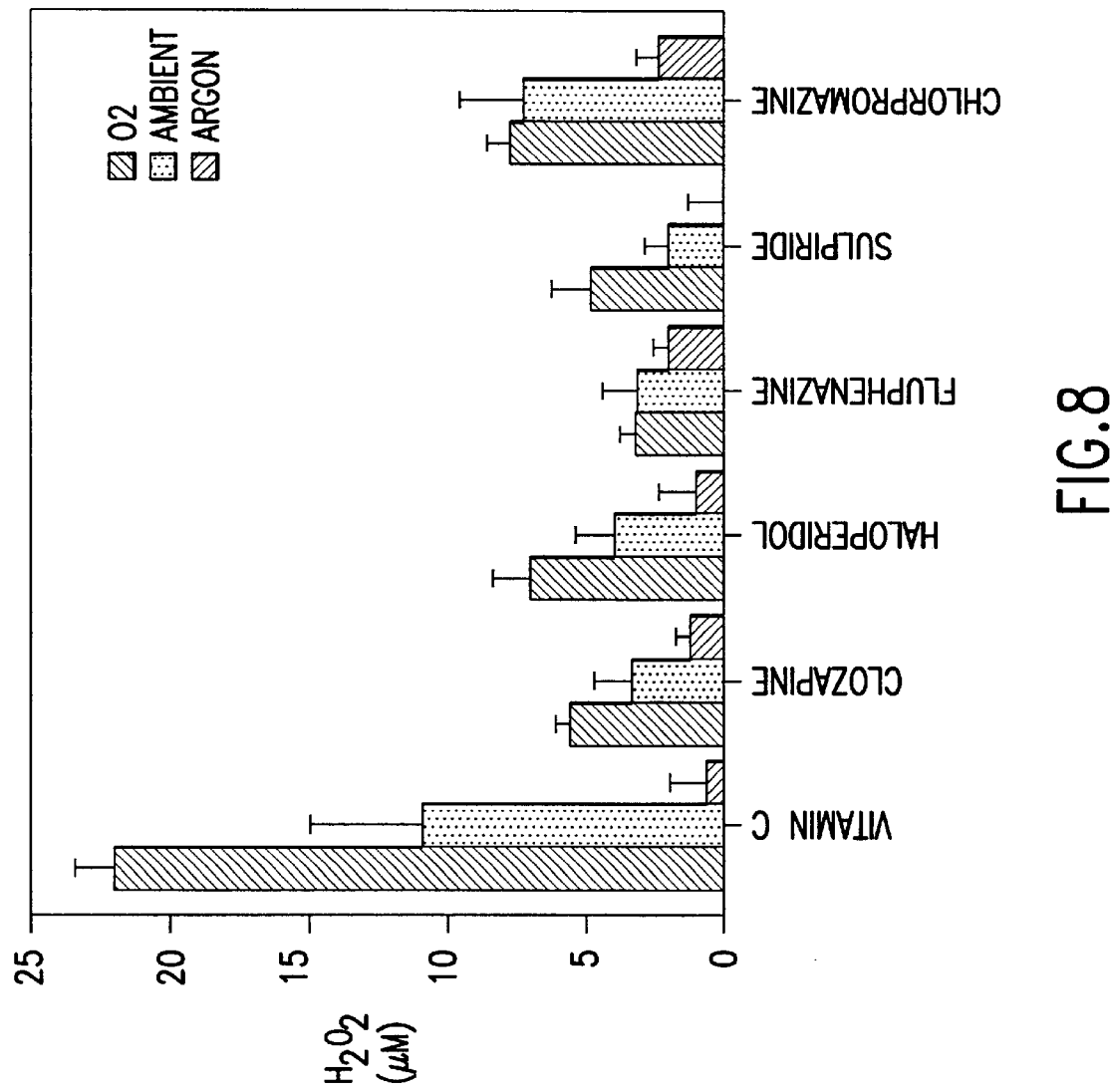
FIG. 8 shows that oxygen augments and argon attenuates the production of hydrogen peroxide production by Vitamin C and antipsychotic drugs. The data were generated using the methods disclosed in Example 1(b).

In addition, the capacity of antipsychotics to generate hydrogen peroxide is dependent on oxygen, i.e. oxygen augments the production of hydrogen peroxide by antipsychotics and argon, which expels oxygen in the reaction, attenuates the production of hydrogen peroxide. (FIG. 8.)

Generation of hydroxyl radical

The reduction by antipsychotics of copper (II) to copper (I) may promote an environment which enhances the production of hydroxyl radicals and contributes to oxidative stress in TD. Consequently, conventional antipsychotics generate hydroxyl radicals by Fenton chemistry which may damage striatal neurons. (FIG. 9.) Therefore, brain copper homeostasis may be a variable that influences the ability of antipsychotics to cause damage to striatal neurons. Copper concentrations in the striatum are stringently regulated by energy-dependent mechanisms, and mutations of a Cu-ATPase cause Wilson's disease, another neurodegenerative striatal disorder.

Figure 10:
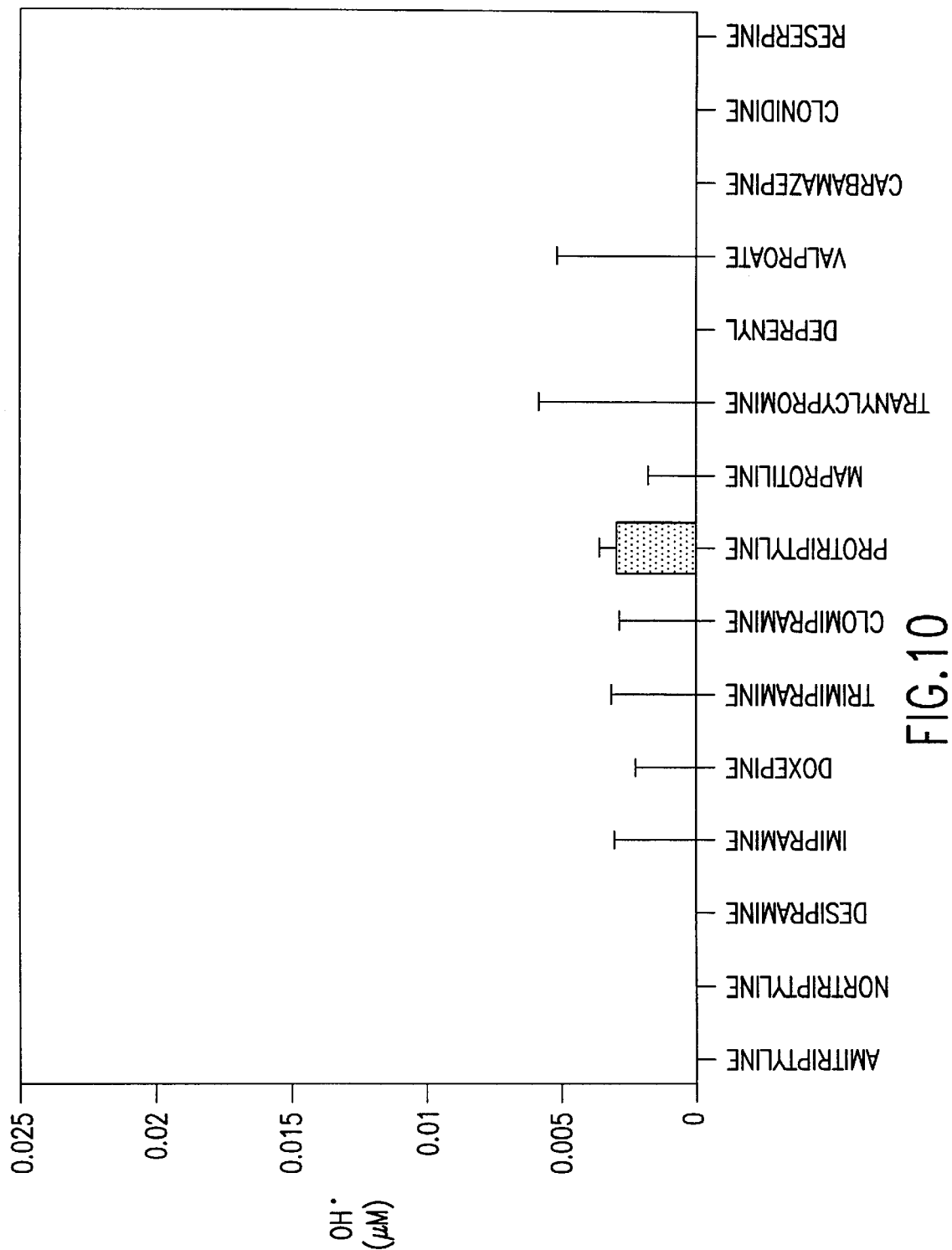
FIG. 10 shows the production of hydroxyl radical by non-antipsychotic psychotropic drugs. The data were generated using the methods disclosed in Example 1(c).

Interestingly, clozapine, antidepressants and other psychotropics did not generate hydroxyl radicals consistent with their low risk of causing TD. (FIGS. 9 and 10.) The inability of clozapine to generate hydroxy radicals in vitro may explain its lower propensity to produce TD.

We have found that clozapine may have superoxide dismutase and catalase activities. Thus, clozapine appears to be atypical of antipsychotic drugs in that, while it reduces Cu(II) ions (FIG. 1), this drug may also scavenge superoxide ions and hydrogen peroxide before appreciable quantities of hydroxyl radicals are formed.

Taken together, the ability of antipsychotics to produce hydrogen peroxide, and consequently hydroxyl radical, depend on the presence of copper and oxygen. The oxidative damage cascade is summarized in FIG. 11. Our findings strongly suggest the redox activity of antipsychotics may underlie the pathogenesis of TD.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method for determining whether a candidate compound induces tardive dyskinesia comprising:
    (a) contacting said candidate compound with a metal ion with a standard reduction potential between 0 and 2.0 E°/V,
    (b) assaying for the production of one or more intermediates or products of reactions associated with the reduction of said metal ion, and
    (c) comparing the production of said intermediates or products to a standard production in a standard reaction mixture, wherein a significant increase over the standard indicates that the candidate compound induces tardive dyskinesia when administered to an animal.

2. The method of claim 1, wherein the metal ion is Cu(II).

3. The method of claim 1, wherein the reaction product assayed is hydrogen peroxide.

4. The method of claim 1, wherein the reaction product assayed is hydroxyl radical.

5. The method of claim 1, wherein the reaction product assayed is superoxide anion.

6. The method of claim 1, wherein the reaction product assayed is reduced reducible substrate.

7. The method of claim 1, wherein the ability of the candidate compound to induce tardive dyskinesia is confirmed by animal testing.

8. The method of claim 1, wherein assaying for reaction product(s) is performed using a high-throughput assay.

9. The method of claim 8, wherein the reaction product is determined calorimetrically.

10. The method of claim 8, wherein the reaction product is determined fluorometrically.

11. The method of claim 8, wherein the assay is performed using samples contained in a multicontainer carrier.

12. The method of claim 8, wherein said candidate compound is an antipsychotic drug.

13. A method for determining whether a candidate compound induces tardive dyskinesia comprising:
   (a) incubating a candidate compound with a metal ion with a standard reduction potential between 0 and 2.0 E°/V, and
   (b) assaying for the production of a reactive oxygen species, whereby a determination of whether the reactive oxygen species has been produced is made by comparison to a standard reaction mixture, wherein a significant increase over the standard indicates that the candidate compound induces tardive dyskinesia when administered to an animal.

14. The method of claim 13, wherein the reactive oxygen species is superoxide anion.

15. The method of claim 13, wherein the reactive oxygen species is hydroxyl radical.

16. The method of claim 13, wherein the reactive oxygen species is hydrogen peroxide.

* * * * *

UNITED STATES PATENT AND TRADEMARK OFFICE
CERTIFICATE OF CORRECTION

PATENT NO. : 6,316,269 B1
DATED : November 13, 2001
INVENTOR(S) : Tsai et al.

It is certified that error appears in the above-identified patent and that said Letters Patent is hereby corrected as shown below:

<u>Column 15,</u>
Line 16, please delete "calorimetrically" and insert therein -- colorimetrically --.

Signed and Sealed this

Twenty-sixth Day of March, 2002

Attest:

JAMES E. ROGAN
*Attesting Officer*   *Director of the United States Patent and Trademark Office*